United States Patent [19]
Massaro et al.

[11] Patent Number: 5,998,486
[45] Date of Patent: Dec. 7, 1999

[54] TREATMENT OF EMPHYSEMA WITH RETINOIC ACID OR OTHER RETINOIDS BY INDUCING FORMATION OF GAS-EXCHANGE UNITS (ALVEOLI)

[75] Inventors: Gloria Massaro; Donald Massaro, both of Washington, D.C.

[73] Assignee: Georgetown University School of Medicine, Washington, D.C.

[21] Appl. No.: 09/110,852

[22] Filed: Jul. 7, 1998

Related U.S. Application Data

[60] Provisional application No. 60/052,791, Jul. 8, 1997.
[51] Int. Cl.$^6$ ..................................................... A61K 31/07
[52] U.S. Cl. .............................................................. 514/725
[58] Field of Search ............................................... 514/725

[56] References Cited

PUBLICATIONS

Massaro et al., American Journal Physiology, 270/2, L305–L310 Feb. 1996.
Sklan et al., Lung, 168(6), 323–32 1990.

*Primary Examiner*—Phyllis G. Spivack
*Attorney, Agent, or Firm*—Burns, Doane, Swecker & Mathis, LLP

[57] ABSTRACT

This invention relates to the use of retinoic acid, its esters and analogues thereof, for treatment of emphysema. The method comprises administration of a composition containing an effective amount of a retinoic acid, or an ester or an analoge thereof, to induce alveolar formation.

5 Claims, No Drawings

TREATMENT OF EMPHYSEMA WITH RETINOIC ACID OR OTHER RETINOIDS BY INDUCING FORMATION OF GAS-EXCHANGE UNITS (ALVEOLI)

This application takes priority from U.S. Provisional Patent Application 60/052,791, filed Jul. 8, 1997.

This work was supported in part by the national Heart, Lung and Blood Institute grants HL-37666 and HL-20366. Certain rights in the government of the United States apply to this invention.

FIELD OF THE INVENTION

This invention relates to the treatment of emphysema using retinoic acid, their esters and analogues thereof.

BACKGROUND OF THE INVENTION

Pulmonary emphysema is a common disease in which destruction of the lung's gas-exchange structures (alveoli) leads to inadequate oxygenation, disability and, frequently, death. Lung transplantation has previously provided the only means of remediation.

Alveoli are formed by the developmentally regulated subdivision of saccules that constitute the gas-exchange region of the immature lung. The molecular signals responsible for the formation of septa and for their spacing are poorly understood. However, in the rat retinoids may play a key regulatory role. Fibroblasts rich in vitamin A (retinol) storage granules occupy a large fraction of the alveolar wall when septa are being formed. During the same period, the concentration of cellular-retinol binding protein I, cellular retinoic acid-binding Protein I, and nuclear retinoic acid receptor-τ mRNA peak in the lung. Treatment with dexamethasone, a glucocorticosteroid hormone, prevents septation in a seemingly irrevocable fashion, and diminishes the expression in the lung of cellular retinol-binding protein and retinoic acid receptor-β mRNA.

The use of all-trans retinoic acid for treatment of diseases relating to growth and tissue maintenance has previously been known. Retinoic acid receptors belong to a family of nuclear receptors that includes receptors for steroids, thyroid hormone, and calcitriol. It has previously been disclosed that retinoic acid prevents inhibition of alveoli in rats arising from exposure to dexamethasone. (Am. J. Physiol. 270: L305–L310 (1996)). There is no teaching therein regarding use of retinoic acid for treatment of emphysema.

U.S. Pat. No. 3,171,781 teaches use of vitamin A and guaiacol for treatment of contagious "air sac disease" in fowl. It is not clear what the pathology or nature of the infectious agent of the disease condition might have been. There is no teaching therein regarding retinoic acid or treatment of emphysema.

U.S. Pat. No. 4,606,920 teaches use of vitamins A and C for treatment of inflammatory changes in the bronchial mucosa. There is no teaching seen therein regarding treatment of diseases involving the alveoli.

U.S. Pat. No. 5,534,261, which is incorporated herein in its entirety as though fully copied herein, teaches use of retinoic acid to prevent formation of adhesion between organ surfaces in body cavities, especially in the peritoneal cavity. No teaching of use for treatment of emphysema is seen therein.

U.S. Pat. No. 5,556,611, which is incorporated herein in its entirety as though fully copied herein, teaches use of retinoic acid and esters thereof in the form of aerosols for treatment of mucosal diseases. Diseases to be treated by use of such aerosols include bronchial carcinoma, acute and chronic bronchitis, acute and chronic functional disturbances due to impairment of the trachealbronchial epithelium following inhalation of dusts and gases, bronchopulmonary dysplasia of newborns and carthagena syndrome. There is no suggestion therein that retinoic acid, its esters or analogues thereof can be administered for treatment of emphysema, which arises from destruction of the lung alveoli.

DESCRIPTION OF THE INVENTION

This invention relates to the use of retinoic acid, its esters and analogues thereof for treatment of emphysema. Retinoic acid and its analogues are lipophilic compounds and may be administered by any means known in the art for systemic administration of lipophilic medicinals, including oral and parenteral administration. The method comprises administration of a composition containing an alveoli formation-inducing effective amount of a retinoic acid, its esters and analogues of retinoic acid.

Materials and Methods:

Production of Emphysema and Treatment with All-trans Retinoic Acid. Porcine pancreas elastase (2.0 units·g$^{-1}$ body mass) or an equal volume of saline was instilled into the trachea of anesthetized adult male Sprague-Dawley rats, which were killed 25 days later. Other rats were treated with saline or elastase as just described and used twenty-five days later to form three groups. Rats initially treated with saline (Group 1), and some rats initially treated with elastase (Group 2), were begun on daily intraperitoneal injections of cottonseed oil containing all-trans retinoic acid. Other rats initially treated with elastase were begun on daily intraperitoneal injections of all-trans retinoic acid (500 μg·kg$^{-1}$) dissolved in cottonseed oil (Group 3). Rats were treated daily for 12 days and killed on day 13.

Fixation, Tissue Sampling, and Tissue Preparation. Rats were anesthetized with xylazine (~10 mg·kg$^{-1}$) and ketamine (~75 mg·kg$^{-1}$) and killed by cutting the abdominal aorta. Cold 2.5% glutaraldehyde in 0.1 M sodium cacodylate, pH 7.4, was infused into the trachea at a transpulmonary pressure of 20 cm H$_2$O. The trachea was ligated, lungs were removed from the thorax, and fixation was continued for 2 h at 0–4° C. Lung volume was measured by volume displacement. Lungs were cut into blocks; blocks were selected for study using a systematic sampling technique. Selected blocks were processed further; we corrected for linear shrinkage and volume changes that occur during postfixation, dehydration, and embedding.

Alveolar airspace was distinguished from alveolar duct airspace by analysis of serially sectioned lung. The selector method, which allows structures to be selected for analysis based on number rather than on size, shape, or orientation, was used to choose alveoli for analysis. The volume of an alveolus was estimated by the point-sampled intercepts method (for references)[5]. The volume of an individual alveolus was calculated as previously described. The number of alveoli per lung was calculated using the identity $$N = \frac{V_L \times Vva}{Va},$$

where VL is lung volume (measured by water displacement), Vva is the volume density of alveolar airspace, and v̄a is the mean alveolar volume. Vva and Sa of the gas-exchange region were determined by point and intersection counting.

Statistical Methods. For each parameter measured or calculated from measurements, values for individual animals were averaged per experimental group, and the SE was calculated. The significance of the difference between two groups was obtained using the Mann-Whitney test. The Kruskal-Wallis test was used when more than two groups were compared and the Mann-Whitney test was then used to compare two populations at a time; the Bonferroni adjustment was used to adjust the significance level to the number of tests performed.

Results:

Treatment with retinoic acid reversed the anatomical characteristics and increased lung volume of elastase-induced emphysema in rats.

In rats killed 25 days after the intratracheal instillation of 0.15 M NaCl (saline) the distance between alveolar walls (Lm) was 71±1.9 µm and alveolar surface area (Sa) 4952±259 cm$^2$ (mean±SE, N=3). Twenty-five days after the instillation of elastase (N=5) Lm was 93±7 µm and Sa 3992±118 cm$^2$ (P<0.03 between groups for the same parameter). The larger Lm and smaller Sa in elastase-treated rats indicate their lungs were emphysematous. Emphysema produced by elastase becomes progressively worse for 1–2 months without spontaneous recovery.

Lung volume was 18% greater in emphysematous rats treated with cottonseed oil, the diluent for RA, (elastase-oil rats) than in rats given saline followed by cottonseed oil (saline-oil rats) or in rats given elastase then RA (elastase-RA rats) (Table 1). Because body mass was the same in all groups (Table 1), and lung volume is proportional to body mass, the larger lungs of elastase-oil rats reflect diminished elastic recoil, a characteristic feature of experimental and human emphysema, rather than lung growth. This effect of elastase on lung volume was completely reversed by treatment with RA (Table 1).

Distance between alveolar walls (Lm), and the volume of an average alveolus (va), were higher and alveolar number (Na) lower in elastase-oil rats than in saline-oil rats (Table 1). After correction for overexpansion of the lung in elastase-oil rats, Lm and $\overline{v}a$ remained larger (P<0.025) than in rats of either other group. Sa was not significantly diminished in elastase-oil rats despite the presence of 45% fewer alveoli because the low elastic recoil allowed overexpansion of the lung. However, Sa per lung volume, a cardinal feature of emphysema[2], was diminished in elastase-oil rats (Table 1). In rats treated with RA $\overline{v}a$, Na, and volume-corrected Sa were the same as in rats not made emphysematous (saline-oil) and were significantly different from the values in elastase-oil rats (Table 1). In saline-oil, elastase-oil, and elastase-RA rats the percentage of alveoli with a volume $\geq 10 \times 10^4$ µm$^3$ (chosen arbitrarily) was, respectively, 20, 64, and 33. These quantitative differences in architecture of the lung's gas-exchange region were appreciated on histological lung sections.

Although diminished recoil allows lung volume to increase, the fairly rigid bony thorax of human adults imposes constraints upon lung enlargement and hence upon the degree to which Sa can be augmented by overexpansion of the lung. In human emphysema the presence of large bullae can also limit the extent to which expansion can increase Sa. Therefore, to increase Sa for therapeutic purposes, a pharmacological agent should ideally induce the formation of alveoli with a high surface-to-volume ratio. Retinoic acid (RA) does that. More numerous alveoli in elastase-RA were found than in elastase-oil rats and this was brought about by the generation of smaller alveoli, i.e. alveoli with a high surface-to-volume ratio, rather than by increasing lung volume (Table 1). That the frequency-distribution of alveoli revealed many fewer large alveoli in elastase-RA rats than in elastase-oil rats, strongly suggests treatment with RA induced the formation of septa from the walls of the large alveoli that resulted from prior destruction of alveolar walls by elastase. The lower lung volume in elastase-RA compared to elastase-oil rats indicates lung recoil increased in rats treated with RA.

TABLE I

Body weight, lung volume, alveolar size and number and surface area in mammals:

| Parameters | Treatments | | |
|---|---|---|---|
| | Saline-oil | Elastase-oil | Elastase-RA |
| Body weight | 410 ± 11 (6) | 403 ± 7 (7) | 404 ± 5 (7) |
| Lung volume, cm$^3$ | 10.0 ± 0.5 (6) | 11.8 ± 0.5 (7) | 10.1 ± 0.3 (7) |
| Lung vol, cm$^3 \cdot$ kg$^{-1}$ | 24.3 ± 0.7 (6) | 28.8 ± 1.4 (7) | 24.9 ± 0.6 (7) |
| Lm, µm | 74 ± 3 (6) | 96 ± 5 (7) | 67 ± 2 (7) |
| $\overline{v}a$, µm$^3 \times 10^{-4}$ | 7.9 ± 0.5 (5) | 19.1 ± 1.6 (5) | 9.3 ± 0.9 (5) |
| Na $\times 10^{-6}$ | 58.8 ± 7.0 (5) | 30.2 ± 2.1 (5) | 55.4 ± 36 (5) |
| Na $10^{-6} \cdot$ kg$^{-1}$ | 143 ± 21.1 (5) | 75.3 ± 4.9 (5) | 136 ± 9.9 (5) |
| Sa, cm$^2$ | 4434 ± 251 (6) | 4222 ± 90 (7) | 4939 ± 136 (7) |
| Sa.lung vol.$^{-1}$, cm$^{-1}$ | 444 ± 12 (6) | 362 ± 16 (7) | 492 ± 10 (7) |

Mean±SE given. Figures in parentheses indicate the number of rats. $\overline{v}a$ denotes the volume of an average alveolus, Na the number of alveoli per rat, Sa the alveolar surface area, and Lm, distance between alveolar walls.

Treatment with retinoic acid caused a marked reduction in the number of large alveoli in rats previously treated with elastase. It was found that treatment with retinoic acid abrogated elastase-induced emphysema. The airspaces were larger and less numerous in lungs of rats who received only the cottonseed oil. Treatment with retinoic acid returned the lung's morphology to that present in rats previously not emphysematous.

As indicated, the active agents of the invention may be administered in any manner used to administer lipophilic agents, and will depend on the mode of administration. Solvents for lipophilic compounds known in the art include (but are not limited to) glycols such as polypropylene glycol, polyethylene glycol, oils and cyclodextrins, especially the intrinsically amorphous cyclodextrins. Other vehicles that should be considered include fatty acid esters of polyoxyethylene sorbatan (Tweens) or sorbitan (Spans) used to prepare oil-in-water emulsions. The active agents, retinoic acids and esters or analogues thereof may also be administered as liposomes. The active agents may be administered in depo agents such as oils. In the instant examples, cotton oil was used.

The therapeutic compositions may also be administered as an inhalant via nebulizer.

Compositions may be administered by any means that will result in uptake into the blood stream, including subcutaneous, intramuscular and intravenous administration. Cyclodextrin inclusion complexes may be administered sublingually or buccally.

A patch for the administration of the active agents may be formulated as adhesive patches containing the drug. For example, the patch may be a discoid in which a pressure-sensitive silicone adhesive matrix containing the active agent may be covered with a non-permeable backing. The discoid may either contain the active agent in the adhesive or may have attached thereto a support made of material such as polyurethane foam or gauze that will hold the active agent. Before use, the material containing the active agent would be covered to protect the patch.

The dosage required will depend on the size, age and condition of the patient. Dosage of about 0.1 µg/kg to 1000 µg/kg would be appropriate, with the higher dosage per kg being appropriate in small mammals and the lower dosage per kg of about 0.1 µg/kg to 1000 µg/kg being appropriate in larger mammals such as humans.

EXAMPLE 1

A patch composed of trilaminate of an adhesive matrix sandwiched between a non-permeable backing and a protective covering layer is prepared in the following manner:

To a pressure-sensitive silicone adhesive composition BIOPSA™ Q7-2920 (Dow Corning Corp., Midland, Michigan, U.S.A.) in cyclohexane (50% w/v) is added sufficient retinoic acid to provide a 0.5% retinoic acid composition. The adhesive is applied to a polyester film to provide in successive layers to provide about 2 mg of active agent per $cm^2$. The film containing the adhesive is then made into patches of 10 $cm^2$. For patches would be covered with a protective layer to be removed before application of the patch. Patches may be prepared containing permeation enhancers such as cyclodextrin, butylated hydroxyanisole, or butylated hydroxytoluene. When the patches are to be applied to thin or abraded skin, there is little need to add a permeation enhancer.

EXAMPLE 2

| Ingredient | w/w % |
| --- | --- |
| ethyl ester of retinoic acid | 20 µg |
| Propylene glycol | .2 ml |
| Saline added to total volume of | 2 ml |

EXAMPLE 3

Saturated aqueous solutions of the sparingly soluble retinoic acid were made by stirring an excess of the RA with water with an aqueous solution (5% weight by weight) of dihydroxypropylcyclodextrin to form cyclodextrin inclusion complexes. (The stirring step required at least one day.) The concentration of the drug in a filtered solution was subsequently determined by spectrophotometry.

The resulting cyclodextrin inclusion complex was dissolved in saline to provide 10 µg retinoic acid for administration sublingually, buccally or by nebulizer.

In order to obtain more prolonged action, it is possible to administer an ester of the retinoic acid. Examples of such esters are the alkyl esters such as methyl, ethyl, propyl and butyl esters. The ester moieties may also have cyclized or aryl groups such as benzyl, hydroxybenzyl and cyclohexyl esters.

What we claim is:

1. A method of treating emphysema by increasing the formation of alveoli in a mammal comprising administration of a composition containing, an effective amount of a retinoic acid or an ester or analog of retinoic acid, in a pharmaceutically acceptable carrier.

2. A method of claim 1 wherein the carrier is a patch.

3. A method of claim 1 wherein the mammal is a human.

4. A method of claim 1 wherein the composition is administered parenterally.

5. A method of claim 1 wherein the composition is administered either buccally, sublingually or by nebulizer.

* * * * *

UNITED STATES PATENT AND TRADEMARK OFFICE
CERTIFICATE OF CORRECTION

PATENT NO. : 5,998,486
DATED : December 7, 1999
INVENTOR(S) : Gloria Massaro et al.

It is certified that error appears in the above-identified patent and that said Letters Patent is hereby corrected as shown below:

Col. 2, line 61
  replace "va"
  with --$\overline{v}$a--.

Col. 3, line 46
  replace "RAva"
  with --Ra, $\overline{v}$a,--.

Col. 4, line 27
  replace "va"
  with --$\overline{v}$a--.

Signed and Sealed this

Twenty-third Day of January, 2001

Attest:

Q. TODD DICKINSON

*Attesting Officer*       *Commissioner of Patents and Trademarks*